(12) United States Patent
Boersma et al.

(10) Patent No.: US 9,170,366 B2
(45) Date of Patent: Oct. 27, 2015

(54) DISTRIBUTED OPTICAL CHEMICAL SENSOR

(75) Inventors: Arjen Boersma, 's-Hertogenbosch (NL); Theodorus Henricus Cornelus Panken, Eindhoven (NL); Lun Kai Cheng, Krimpen a/d IJssel (NL)

(73) Assignee: Nederlandse Organisatie voor toegepast-natuurwetenschappelijk onderzoek TNO, 's-Gravenhage (NL)

( * ) Notice: Subject to any disclaimer, the term of this patent is extended or adjusted under 35 U.S.C. 154(b) by 1008 days.

(21) Appl. No.: 13/141,674

(22) PCT Filed: Dec. 22, 2009

(86) PCT No.: PCT/NL2009/050791
§ 371 (c)(1),
(2), (4) Date: Dec. 13, 2011

(87) PCT Pub. No.: WO2010/074569
PCT Pub. Date: Jul. 1, 2010

(65) Prior Publication Data
US 2012/0081696 A1    Apr. 5, 2012

(30) Foreign Application Priority Data
Dec. 23, 2008 (EP) .................................. 08172778

(51) Int. Cl.
G02B 6/00 (2006.01)
G02B 6/02 (2006.01)
G01D 5/26 (2006.01)
G01N 21/77 (2006.01)

(52) U.S. Cl.
CPC *G02B 6/02* (2013.01); *G01D 5/268* (2013.01); *G01N 21/774* (2013.01); *G02B 6/02104* (2013.01); *G01N 2021/7723* (2013.01)

(58) Field of Classification Search
None
See application file for complete search history.

(56) References Cited

U.S. PATENT DOCUMENTS

| 4,712,865 A * | 12/1987 | Hsu et al. ..................... 385/12 |
| 5,015,843 A | 5/1991 | Seitz et al. |
| 5,380,995 A | 1/1995 | Udd et al. |
| 5,402,231 A | 3/1995 | Udd |
| 5,592,965 A | 1/1997 | Rakieski |

(Continued)

FOREIGN PATENT DOCUMENTS

| CA | 2 332 068 A1 | 9/2001 |
| CN | 101248098 A | 8/2008 |

(Continued)

OTHER PUBLICATIONS

International Search Report corresponding to PCT/NL2009/050791 mailed Jul. 27, 2010, 6 pages.

(Continued)

*Primary Examiner* — Tina Wong
(74) *Attorney, Agent, or Firm* — Kilpatrick Townsend & Stockton LLP

(57) ABSTRACT

The invention relates to a sensor system comprising a waveguide, which waveguide comprises a grating in at least a part of the waveguide, which waveguide further comprises a coating, the coating comprising a polymer, which polymer comprises a chain, in which chain are present an aromatic group and a chemical group selected from the group of sulfonyl groups, carbonyl groups, carbonate groups, fluorocarbon groups, siloxane groups, pyridine groups and amide groups.

16 Claims, 2 Drawing Sheets

(56) References Cited

U.S. PATENT DOCUMENTS

Figure 1:
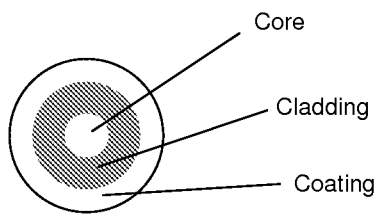

| | | | |
|---|---|---|---|
| 5,841,131 | A | 11/1998 | Schroeder et al. |
| 5,864,641 | A | 1/1999 | Murphy et al. |
| 6,144,026 | A | 11/2000 | Udd et al. |
| 6,978,069 | B1 * | 12/2005 | Taylor et al. ............ 385/122 |
| 7,038,190 | B2 | 5/2006 | Udd et al. |
| 7,340,119 | B1 | 3/2008 | Xu et al. |
| 2003/0156287 | A1 | 8/2003 | Cheng |
| 2004/0115824 | A1 | 6/2004 | Ponce et al. |
| 2005/0105841 | A1 | 5/2005 | Luo et al. |
| 2005/0265649 | A1 | 12/2005 | Da Silva, Jr. et al. |
| 2006/0133766 | A1 * | 6/2006 | Shelnut et al. ............ 385/147 |
| 2011/0200285 | A1 * | 8/2011 | Boersma et al. ............ 385/37 |
| 2012/0081696 | A1 * | 4/2012 | Boersma et al. ............ 356/73.1 |
| 2013/0230656 | A1 * | 9/2013 | Amako et al. ............ 427/387 |

FOREIGN PATENT DOCUMENTS

| | | | |
|---|---|---|---|
| EP | 1 770 388 | A1 | 4/2007 |
| WO | 03/056313 | A1 | 7/2003 |
| WO | WO 2007004743 | A1 * | 1/2007 |
| WO | 2007/065268 | A1 | 6/2007 |

OTHER PUBLICATIONS (Third) Office Action with English translation corresponding to Chinese Patent Application No. 200980157122.9 dated Apr. 22, 2014.

Decision to Grant with English translation corresponding to Russian Patent Application No. 2011130836 dated Jun. 23, 2014.

Kuroiwa, Takaaki et al., "A thin-film polysulfone-based capacitive-type relative-humidity sensor," *Sensors and Actuators B 24-25* (1995) pp. 692-695.

Liu, Xiaomei et al., "Demosntration of etched cladding fiber Bragg grating-based sensors with hydrogel coating," *Sensors and Actuators B 96* (2003) pp. 468-472.

Widera, Justyna et al., "Kinetic behavior of polymer-coated long-period-grating fiber-optic sensors," *Applied Optics* (Feb. 20, 2005) 44(6):1011-1017.

* cited by examiner

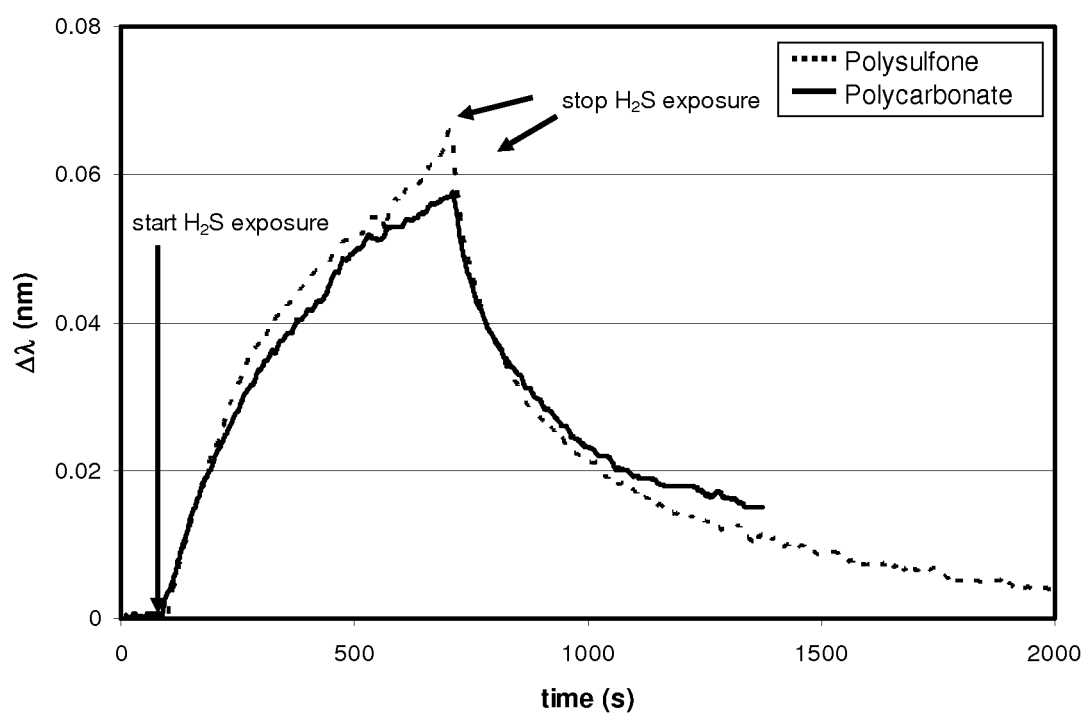
Figure 7. Shift in the Bragg reflection wavelength of a waveguide according to the invention.

DISTRIBUTED OPTICAL CHEMICAL SENSOR

The invention relates to a sensor system, to a waveguide comprising a grating and a sensor material, to the sensor material, to a method of preparing the waveguide, to a sensor system comprising the waveguide, and to the use of the sensor system for measuring an environmental effect.

Optical sensors are sensors of which the sensing principle and optionally the data transfer make use of electromagnetic radiation. Accordingly, optical sensors have a number of advantages over electronic detection systems. Optical sensors are for example more reliable in environments that are difficult to access and/or hazardous to humans, environments such as those found in the oil and gas industry, and are usually not adversely affected by the electromagnetic radiation that is generally produced in for example power cable systems, induction furnaces or equipment for nuclear magnetic resonance measurements, such as MRI or NMR equipment. Other advantages are the easy operation of optical sensors on large distances, their small size, their flexibility and/or the possibility to make a sensor system comprising an array of discrete sensors that all may be read separately from a single optical fibre (a multiplexed sensor system).

Typical sensors that are based on waveguide grating are, e.g., described in detail in U.S. Pat. Nos. 5,380,995, 5,402,231, 5,592,965, 5,841,131, 6,144,026, US 2005/0105841, U.S. Pat. No. 7,038,190, US 2003/156287.

One principle on which such sensors may be based is an axial strain of the waveguide, as a result of an environmental effect that is to be detected, for example by using a coating on the waveguide that deforms under the influence of the environmental effect. An important method via which (a change in) axial strain of the waveguide becomes detectable is to use a grating in the waveguide. When such a grating, guiding a specific spectrum of electromagnetic radiation, stretches or shrinks under the axial strain, the spectral pattern of transmitted radiation and/or the spectral pattern of reflected radiation (i.e. the spectral response) changes. Such changes in the spectral response provide—when measured—quantitative information on the environmental effect. Two examples of a grating are a Fibre Bragg Grating (FBG) and a Long Period Grating (LPG). A multiplexed sensor system can be prepared using a plurality of gratings, in particular FBG's.

For example, US application 2005/0105841 relates to the use of a polyethyleneimine (PEI) monolayer coating on a Long Period Grating waveguide. The coating swells under the uptake of water, which makes a waveguide comprising such coating suitable for measuring relative humidity (RH), based on changes of the refractive index of the coating.

Although it has been widely recognized that optical sensors have a number of advantages over electronic measuring systems, the full potential of optical sensors has not yet been realized. In particular, there is a need for improved sensors for use under extreme conditions, for example under high pressure and/or high temperature. Examples of extreme conditions are conditions that may exist in underground oil or gas reservoirs, or in the equipment that is used to produce oil or gas from these reservoirs. It would in particular be desired to provide an improved sensor for the detection of compounds such as methane, carbon dioxide, hydrogen sulfide or water, e.g. under the conditions as mentioned above. A compound that is to be detected may hereinafter be referred to as 'analyte'.

WO 03/056313 describes an optical sensor that can operate in offshore environments. The sensor relies on the principle that hydrogen can diffuse into an optical fiber, which results in transmission loss though the fibre at specific wavelengths. The quantity of such a loss is a measure for the amount of hydrogen present in the environment. A limitation of this sensor is that the loss of transmission is generally permanent, because the in-diffused hydrogen causes irreversible changes in the fiber.

It is an object of the present invention to provide a novel sensor system.

It is also an object of the present invention to provide a novel waveguide comprising a grating, which waveguide can be used in an optical sensor, in particular a sensor with a detection mechanism that is based on an FBG or an LPG, that can serve as an alternative to known waveguides comprising a grating.

It is in particular an object of the present invention to provide a novel method for preparing a waveguide according to the invention, in particular a method that allows the manufacturing of a multiplexed sensor system in an industrially attractive manner.

It is in particular an object of the invention to provide a novel waveguide that is suitable for use under extreme conditions, such as under conditions that may exist in underground oil or gas reservoirs, or in the equipment that is used to produce oil or gas from these reservoirs.

It is a further object of the invention to provide a novel waveguide that is improved, in particular in that a detection system comprising the waveguide is improved in that it offers at least one of the following advantages: a higher selectivity towards a specific environmental effect, a larger dynamic range, a higher accuracy, a higher robustness, a lower detection limit and a higher sensitivity.

The selectivity of a detection system for measuring a certain environmental condition is the extent to which the detector specifically reacts to a change in a selected environmental condition, without being affected by a change in other conditions.

The dynamic range of a sensor system is the range of a changeable quantity that can be measured with that sensor system, the limits of which range are defined by the smallest and the largest value of the changeable quantity that can be measured with that sensor system.

The accuracy of a detection system is the closeness of a reading or indication of that detection system to the actual value of the quantity being measured.

Robustness is the extent to which a detection system is resistant to changes in the detection system, influences from a specific sample and influences from the environment other than the condition, other than the changes in the condition to be measured. Accordingly, as a system is more stable, the back ground noise will be less and/or fewer artefacts will occur in the measuring signal, such a spikes, base line drift and/or base line shifts.

The detection limit is the lowest measurable change in a environmental condition. It is determined by the signal to noise ratio. In general, the detection limit for a particular substance is set at a signal to noise ratio of 2 (if the noise is represented as peak to peak) or 4 (if the noise is represented as the root of the mean square noise (RMS noise)).

The sensitivity of a detection system is the smallest change in a environmental condition, such as a physical or chemical parameter, that can be detected by the detection system.

It has now been found that one or more of these objects are realised by providing a waveguide having a coating which comprises a polymer comprising specific groups.

Accordingly, the invention relates to a sensor system for detecting a chemical substance (analyte), comprising a waveguide, which waveguide comprises a grating in at least a part of the waveguide, which waveguide further comprises a coating, the coating comprising a polymer, which polymer comprises a chain having an aromatic group and a further chemical group selected from the group of sulfonyl groups, carbonyl groups, carbonate groups, fluoro carbon groups, siloxane groups, pyridine groups and amide groups.

Such a sensor system may in a preferred embodiment be used under extreme conditions, such as under conditions that may exist in underground oil or gas reservoirs, or in the equipment that is used to produce oil or gas from these reservoirs.

In a preferred embodiment, the chain further comprises imide groups. In another preferred embodiment, these imide groups may also be present in the polymeric coating in a different chain, such that the polymeric coating is a blend of two or more polymers. In a specific embodiment, the chain further comprises oxygen atoms. The presence of sulfonyl groups, carbonyl groups, carbonate groups, amide groups, fluoro carbon groups, siloxane groups, pyridine groups, imide groups or oxygen atoms in the chain is considered beneficial for improved interaction with an analyte of interest, thereby improving, e.g. the sensitivity and/or the dynamic range.

Preferably, a sensor system according to the invention comprises a source for providing electromagnetic radiation and a photo-detector.

The invention further relates to a waveguide, comprising a grating in at least a part of the waveguide, which waveguide comprises a coating, the coating comprising a polymer, which polymer comprises a chain having an aromatic group and a chemical group selected from the group of sulfonyl groups, carbonyl groups, carbonate groups, fluoro carbon groups, siloxane groups, pyridine groups and amide groups. In a preferred embodiment, the chain further comprises imide groups. In a specific embodiment, the chain further comprises oxygen atoms.

In the present disclosure, the term waveguide is used for optical waveguides. An optical waveguide is a physical structure that guides electromagnetic waves in at least part of the optical spectrum, i.e. in at least part of the spectrum formed by the infrared, visible and ultraviolet ranges of the electromagnetic spectrum.

Usually, a waveguide is of elongate form. In general, a waveguide is cylindrical, in particular with a circular cross-section. A waveguide generally comprises an assembly of a core and a cladding covering the core. The core as well as the cladding usually have a substantially circular cross-section. The center of the cross-section of the cladding usually coincides with the center of the cross-section of the core (FIG. 1). As discussed below, in specific embodiments the cross-section of the core and/or the cladding may be different. With a cross-section of the waveguide is meant a section through the waveguide that is a plane that is perpendicular to the longitudinal direction of the waveguide.

Common types of waveguides include optical fibres, e.g. as referred to in the above cited prior art, and rectangular waveguides. Waveguides are commercially obtainable from various sources. Manufacturing and applications can be found in the Encyclopedia of Laser Physics and Technology (http://www.rp-photonics.com/encyclopedia.html). Fibre Bragg Gratings are supplied by FOS&S, Geel, Belgium.

In the present disclosure, with "grating" is meant a periodic variation of the refractive index of waveguide material in a segment of a waveguide core. A grating reflects particular wavelengths of electromagnetic waves and transmits other wavelengths, and can be used as an inline optical filter or as a wavelength-specific reflector. A grating in a waveguide according to the invention may in particular be a Fibre Bragg Grating (FBG).

As indicated above, the coating of the waveguide comprises a polymer; a polymer is a substance of which the molecules, in particular organic molecules, are built up from a plurality of monomeric units. The polymer of the coating is usually built up from at least 10 monomeric units, preferably at least 50 monomeric units, at least 100 monomeric units, or at least 250 monomeric units. The upper limit of the polymer is not particularly critical and can be, for instance, 1 000, 10 000, 50 000, or more than 50 000 monomeric units. The monomeric units may be the same (a homopolymer) or the polymer may be composed of two or more different monomers (a copolymer).

The polymer of the coating may be branched or linear. The polymer may be cross-linked or uncrosslinked. In case the polymer comprises more than one chain per polymer molecule, typically at least the main-chain has an aromatic group and a group selected from the group of sulfonyl groups, carbonyl groups, carbonate groups, imide groups, fluoro carbon groups, siloxane groups, pyridine groups and amide groups. Side-chains may also comprise such groups. In case the polymer is such that it contains a plurality of (major) chains without one chain being the main chain (as may be the case in e.g. hyperbranched polymers) preferably most or all of said chains have an aromatic group and a group selected from the group of sulfonyl groups, carbonyl groups, carbonate groups, imide groups, fluoro carbon groups, siloxane groups, pyridine groups and amide groups. Thus, it should be understood that said groups form part of the backbone of the polymer and the polymer is thus distinguishable from a polymer wherein an aromatic group and a group selected from the group of sulfonyl groups, carbonyl groups, carbonate groups, imide groups, fluoro carbon groups, siloxane groups, pyridine groups and amide groups are pendant.

A preferred aromatic group in a chain of said polymer is a phenyl group, preferably a p-phenylene group, which may comprise substituents. Other preferred aromatic groups are selected from the group of naphthalene groups.

In a preferred embodiment, the sulfonyl groups, carbonyl groups, carbonate groups, imide groups, siloxane groups, pyridine groups respectively amide groups are directly attached to the aromatic group. Thus, a preferred polymer molecule may comprise the following structure: —[Ar—X—]$_n$. Herein 'n' is an integer representing the number of monomeric units. 'Ar' represents the aromatic group, each X independently comprises a group selected from sulfonyl groups, carbonyl groups, carbonate groups, imide groups, siloxane groups, pyridine groups and amide groups, with the proviso that at least one of the X's represents a sulfonyl group, a carbonyl group, a carbonate group, a siloxane group, a pyridine group or an amide group.

In a further embodiment, at least one X represents a organofluorine group. Organofluorine groups (also known as fluoro carbons) are groups comprising carbon, fluorine and optionally one or more other groups, in particular one or more hydrogen atoms. In particular, the organofluorine may be represented by the formula -$C_mF_kH_l$—, wherein m is an integer, e.g. in the range of 1-10, in particular in the range of 2-6. As generally known in chemistry, the values for k and l depend on the value for m and the number of unsaturated carbon bonds. The integer k is in the range of 1 to 2m, the integer l is in the range of 0 to 2m-1, with the proviso that the sum of k and l is 2m (if no unsaturated bonds are present) or less (if one or more unsaturated bonds are present). In particular the —$C_mF_kH_l$— group may be a hydrofluoroalkyl or a perfluoroalkyl. In case of a hydrofluoroalkyl the sum of k+l equals 2m and k and l are both at least 1. In case of a perfluoroalkyl k equals 2m and l is 0. A preferred perfluoroalkyl is hexafluoroisopropyl. The number of fluorine atoms in a organofluorine is preferably equal to or higher than the number of hydrogen atoms, for improved interaction with an analyte. Two aromatic groups in the polymer chain can also be separated by an oxygen molecule. Thus, a preferred polymer may comprise the following structure: —[Ar—O—Ar—X—]$_n$, wherein X and n are as identified above. Two aromatic groups in the polymer chain can also be separated by an analyte specific group (i.e. group capable of selectively interacting with an analyte of interest, thereby causing a change in the polymer material), such as hexafluoroisopropyl, another alkyl comprising fluorine groups, or isopropyl, siloxane or pyridine. Thus, a preferred polymer may comprise the following structure: —[Ar—C(CF$_3$)$_2$—Ar—X—]$_n$, wherein X and n are as identified above.

In a preferred embodiment, the polymer is selected from the group of polysulfones comprising aromatic groups in the chain and polycarbonates comprising aromatic groups in the chain. Any of these may in particular be used for a waveguide of a detection system for detecting H$_2$S. In a specific embodiment, the polymer also comprises imide groups in the chain or the polymer is a blend of a polymer comprising at least one polymer selected from the group of polysulfones comprising aromatic groups in the chain and polycarbonates comprising aromatic groups in the chain and further comprising a polymer comprising imide groups and aromatic groups in the chain.

Such an embodiment is in particular preferred for a high sensitivity and/or a high temperature resistance.

In particular, the polysulfone may be selected from the group of poly(diphenyl sulfones). Preferred polysulfones are poly(oxy-1,4-phenylenesulfonyl-1,4-phenyleneoxy-1,4-phenyleneisopropylidene-1,4-phenylene) and poly(oxy-1,4-phenylenesulfonyl-1,4-phenylene).

In particular, the polycarbonate may be selected from the group of poly(diphenyl carbonates). Preferred polycarbonates are poly(oxycarbonyloxy-1,4-phenyleneisopropylidene-1,4-phenylene) and poly(oxycarbonyloxy-1,4-phenylene-hexafluoroisopropylidene-1,4-phenylene).

In particular, the polyimide may be selected from the group of aromatic fluorocarbon polyimided. A preferred polyimide is poly(4,4'-(sulfonylbis(4,1-phenyleneoxy)) dianiline-co-4, 4'-(hexafluoro-isopropylidene)diphthalic anhydride).

A preferred polyamide is poly(trimellitic anhydride chloride-co-4,4'-diaminodiphenylsulfone).

The silixone may in particular be a dialkylsiloxane, which alkyl may comprise one or more substituents, e.g. on ore more fluorine atoms. A preferred siloxane is dimethylsiloxane. The siloxane may advantageously be present in a detection system for CO$_2$.

A preferred polysiloxane polymer in a coating of a sensor system of the invention is polysiloxane, preferably poly (1,3-bis(3-aminopropyl) tetramethyldisiloxane-co-4,4'-(hexafluoro-isopropylidene) diphthalic anhydride).

For H$_2$S detection, poly(4,4'-(sulfonylbis(4,1-phenyleneoxy)) dianiline-co-4,4'-(hexafluoro-isopropylidene) diphthalic anhydride) and poly(oxy-1,4-phenylenesulfonyl-1,4-phenyleneoxy-1,4-phenyleneisopropylidene-1,4-phenylene) are particularly suitable.

If desired, the selectivity of the coating for a specific analyte may be enhanced by including one or more functional groups that are capable of specifically interacting with the analyte to be detected. Such functional group having affinity for a specific analyte may be included in the chain, or be pendant from the chain. For example, the polymer may comprise amine side-chains, in particular for an increase in interaction with hydrogen sulfide. The polymer may comprise halogenated alkyl moieties, e.g. hexafluoro propyl groups, which may in particular be present in the chain. Such groups increase interaction with polar analytes and may in particular increase the dynamic range and/or the sensitivity.

The polymer of the coating may comprise cross-links. If cross-links are present, a typical cross-linking degree is 1 to 50 cross-links per 100 monomer units. The polymeric chains may be cross-linked by reacting the polymer with a cross-linker (i.e. a compound capable of initiating the cross-link reaction or a multi-functional monomer, for example 1 to 30 wt % of crosslinker, based on the total weight of the polymer before crosslinking.

Several cross-linkers are known in the art. Preferred examples of crosslinkers are polyfunctional peroxides.

It is also possible to prepare a crosslinked polymer by polymerising a monomer mixture comprising at least one monomer for forming the aliphatic chain and at least one multifunctional monomer for forming the crosslinks. The concentration of multifunctional monomer may for instance be chosen in the range of 1 to 30 wt % based on total monomers. In the case of polyimides, preferred examples of crosslinkers are polyfunctional anhydrides or amines.

In an advantageous embodiment, the presence of aromatic group(s) and said further chemical group(s) in a polymer according to the invention results in a high stiffness and high temperature resistance. Accordingly, a coated waveguide according to the invention is suitable for use under extreme conditions such as a high pressure and/or a high temperature. In particular, in an embodiment wherein the chain of the polymer comprises imide groups, the polymer has a particularly high temperature resistance.

The polymer coating of the present invention is usually resistant to temperatures higher than 100° C., preferably higher than 150° C., in particular higher than 180° C. Resistance against high temperatures means that the softening temperature or glass transition temperature ($T_g$) is higher than the temperatures given above. In particular, resistance against high temperatures means that the temperature at which chemical degradation of the coating occurs is higher than the temperatures given above. For a high temperature resistance, in particular a polymer selected from the group consisting of polysulfones (polyethersulfones, polyphenylsulfones), polycarbonates, polyketones, polyimides, polysiloxanes and polyamides is suitable.

A sensor system according to the invention may advantageously be used under extreme conditions, such as under conditions that may exist in underground oil or gas reservoirs, or in the equipment that is used to produce oil or gas from these reservoirs. Such extreme conditions include high temperature (which may be over 50° C., over 70° C. or even over 100° C., e.g. up to 250° C., up to 200° C. or up to 150° C., depending on the depth), high pressure (which may be over 50 bar, over 100 bar, e.g. up to 200 bar or up to 150 bar, depending on the depth) and/or high salt concentration (e.g. saturation or oversaturation with NaCl).

Preferably, polymers according to the invention are amorphous, or at least generally substantially amorphous. The $T_g$ of the polymer is usually 100° C. or more, preferably 150° C. or more, more preferably 180° C. or more.

The $T_g$ as used herein is the $T_g$ as determined from the second heating curve obtained by Differential Scanning calorimetry (DSC) using a heating rate and a cooling rate of 10° C./min (10 mg of sample under a nitrogen atmosphere).

A chain of a polymer according to the invention may comprise oxygen atoms. The presence of oxygen in the chain, in particular as an ether unit, provides a higher sensitivity and/or a higher dynamic range of the sensor system.

A coating layer according to the invention usually has a thickness of at least 0.5 µm, preferably of at least 10 µm, more preferably of at least 20 µm. Usually, the thickness is 200 µm or less, in particular, at most 100 µm, preferably 75 µm or less, more preferably 50 µm or less. A relatively thin layer is advantageous for a short response time, a relatively thick layer is advantageous for a high sensitivity.

In a specific embodiment, a waveguide according to the invention has a barrier layer that is impermeable to hydrogen (gas). The permeability is for example less than $10^{15}$ molecules/s.cm.atm$^{1/2}$. Such layer is preferably present between the cladding of the waveguide and the polymeric coating, and may protect the waveguide from harmful effects of the hydrogen. For example, such a layer may comprise a material selected from the group of carbon, silicon carbide, silicon nitride and metals.

The invention is advantageous in that it is possible to provide a coating that can reversibly absorb an analyte of interest in order to perform a continuous measurement of the presence of the analyte. With a continuous measurement is meant a measurement in a non-cumulative way. For example, in a continuous measurement it is possible to measure fluctuations of an environmental effect, such as fluctuations in the concentration of a certain chemical. This is in contrast to a cumulative way of measuring, wherein the total amount of the chemical is observed (like in a dosimeter), i.e. only one or more increases can be observed.

The ability of a sensor system according to the invention to perform a continuous measurement is demonstrated in FIG. 7 (see also Example 1). Herein is shown, that after the exposure to a certain analyte had been stopped, the spectral response (i.e. the shift in the Bragg reflection wavelength) tended to revert back to the pattern before the exposure of the polymer to the certain analyte started.

In the field of oil exploration and in the field of gas exploration, it is highly preferred to monitor the downhole environment for a long period of time without replacing the sensor system. In such applications, it is advantageous to use a sensor system according to the invention, because such a system can perform continuous measurements and has a high resistance against the conditions that may be present in downhole environments such as oil wells or gas wells.

A sensor system according to the invention may in particular be used for detecting in an environment at least one analyte selected from the group of alkanes (in particular methane, ethane, or propane), carbon dioxide, hydrogen, hydrogen sulphide, water, carbon monoxide, oxygen, hydrogen cyanide and ammonia, in particular hydrogen sulphide and carbon dioxide.

In a specific embodiment, a (multiplexed) sensor system according to the invention is used for detecting a water-oil or water-gas interface, for monitoring the displacement of such interfaces or for monitoring the conditions in the proximity of such interfaces. This can be done by using a waveguide of which the coating is capable of interaction with a component of the water phase (e.g. water, NaCl) or a component of the oil/gas phase (e.g. $H_2S$, $CH_4$). The interface may in particular be monitored in (underground) an oil/gas reservoir.

A sensor of the invention is in particular suitable for detecting a gaseous or vaporous analyte.

In a specific embodiment, a waveguide according to the invention comprises a plurality of gratings, which are typically spatially apart, preferably 2-500, in particular 2-100 gratings. A waveguide having a plurality of gratings may be used in a multiplex detection system, wherein the spatially apart grating may be provided with a coating capable of interacting with the environmental effect, such as the presence of an analyte of which the presence is to be detected In particular for a fibre Bragg grating, it is useful to have a plurality of gratings. This allows each grating on the waveguide to be designed in such a way that it creates a spectral response that is unique with respect to the other gratings on the waveguide. This allows, for instance, a single waveguide to be used to measure an environmental effect at a plurality of places. From a change in a specific unique spectral response (measured at one or both of the ends of a waveguide) it will be clear in the vicinity of which grating an environmental effect has changed. In particular in case different gratings are coated with different polymeric materials, adapted to respond towards a change in different environmental effect, this also allows the use of a single waveguide to measure a multitude of environmental effects.

In a specific embodiment, a waveguide according to the invention comprises a multitude of gratings, at least part of which are present as pairs. If desired, the gratings of a pair can be spatially apart. A first grating of each pair may be used to measure (a change) in a certain environmental effect, and a second grating of each pair is uncoated or is coated with a coating that is insensitive, or at least not sensitive to a measurable extent, to the environmental effect to be measured with first grating of the pair. The second grating may be used for monitoring the temperature, and may in particular be used to correct for the influence of temperature on the first grating of the pair.

In a further embodiment, a grating is partly coated (in the longitudinal direction of the waveguide) with a coating that is sensitive to a measurable extent to the environmental effect to be measured. The grating is e.g. coated for only about half of its length. Accordingly, the coated part of the grating then in essence forms the first grating and the part of the grating that is not coated with the sensitive coating forms the second grating.

Usually, a waveguide according to the invention comprises an assembly of a core and a cladding. The electromagnetic radiation used for measuring predominantly propagates through the core. The cladding usually encloses the core; it may protect the core, and/or aid in the propagation of radiation through the core.

In a preferred embodiment, the coating comprises particles. In particular, the particles may be embedded in the polymer comprising a chain, in which chain are present an aromatic group and a chemical group selected from the group of sulfonyl groups, carbonyl groups, carbonate groups, fluoro carbon groups, siloxane groups, pyridine groups, and amide groups.

As used herein, particles include particles which are typically composed of solid or semi-solid materials. Typically, the (weight) average diameter of such particles ranges from approximately 10 nm to approximately 10 µm. A preferred average diameter is in the range of 50-5000 nm, in particular in the range of 50-1000 nm. The average particle diameters are determinable by scanning electron microscopy (SEM). Particles having a average diameter of less than 500 nm are referred to herein as nanoparticles. As will be understood by the skilled person, the size of the particles usually is equal to or less than the thickness of the coating.

In a preferred embodiment, a coating of a waveguide includes particles, in particular nanoparticles, that are capable of absorbing an analyte of interest (i.e. absorbent particles). It is contemplated that the particles swell upon absorption, which results in deformation of the coating, in an increase of axial strain in the waveguide, and ultimately in a change in the spectral response of the electromagnetic radiation that is sent through the waveguide.

Further, in an advantageous embodiment, the particles are elastomeric particles. Typically, such (nano)particles that are capable of absorbing an analyte of interest are made of a material that has a low stiffness (e.g. E-modulus<100 MPa) and/or a low glass transition temperature (e.g. $T_g$<50° C.) (compared to the polymer comprising a chain, in which chain are present an aromatic group and a chemical group selected from the group of sulfonyl groups, carbonyl groups, carbonate groups, fluoro carbon groups, siloxane groups, pyridine groups, and amide groups) and is not suitable for the same purpose when the particles are not embedded in the polymeric coating.

In an advantageous embodiment, selectivity is enhanced by the introduction of (polymer) (nano)particles that are capable of selectively absorbing the analyte. In this case, a high extent of absorption of the analyte in the nanoparticles is combined with a high diffusion speed (mobility) of the analyte in the coating polymer.

In a particularly advantageous embodiment the particles, which may be nanoparticles, comprise a copolymer of a polyether and polyamide (e.g. Pebax polymers, for instance as available from Arkema) or a fluorocarbon composition (e.g. fluoroalkyl(meth)acrylates, PTFE, FEP, PFA, MFA, etc.). Such particles may in particular be suitable for use in a coating of a waveguide for use in the detection of $H_2S$.

In a further advantageous embodiment, said coating of the waveguide comprises particles, preferably nanoparticles, selected from the group of metal-organic frameworks (MOF's) particles. MOF's, also called "hybrid crystallised solids", are coordination compounds with a hybrid inorganic-organic framework comprising metal ions or semi-metal ions and organic ligands coordinated to the metal ions. These materials are organised as mono-, bi- or tri- dimensional networks wherein the metal clusters are linked to each other by spacer ligands in a periodic way. These materials generally have a crystalline structure and are usually porous. MOF's are in particular suitable for their good adsorption properties with respect to a gaseous analyte, for instance $H_2$, a hydrocarbon gas (such as $CH_4$) or $CO_2$.

The metal or semi-metal ions generally have a valence of at least +2. Common ligands include the conjugated bases of organic acids, such as bidentate carboxylates (e.g. oxalate, malonate, succinate, glutarate, phtalate, isophtalate, terephtalate), tridentate carboxylates (e.g. citrate, trimesate).

In a specific embodiment, the MOF is represented by the formula $M_nO_kX_iL_p$, wherein
  each M is independently selected from the group of metal and semi-metal ions, in particular selected from the group consisting of $Ti^{4+}$, $Zr^{4+}$, $Mn^{4+}$, $Si^{4+}$, $Al^{3+}$, $Cr^{3+}$, $V^{3+}$, $Ga^{3+}$, $In^{3+}$, $Mn^{3+}$, $Mn^{2+}$, $Mg^{2+}$ and combinations thereof;
  m is 1, 2, 3 or 4, preferably 1 or 3;
  k is 0, 1, 2, 3 or 4, preferably 0 or 1;
  i is 0, 1, 2, 3 or 4, preferably 0 or 1;
  p is 1, 2, 3 or 4, preferably 1 or 3;
  O is oxygen
  each X is independently selected from the group of anions, in particular from the group of monovalent anions, more in particular from the group consisting of $OH^-$ $Cl^-$, $F^-$, $I^-$, $Br^-$, $SO_4^{2-}$, $NO_{3-}$, $ClO_{4-}$ $PF_{6-}$, $BF_{3-}$, $—(COO)_{n-}$, $R^1—(SO_3)_{n-}$, $R^1—PO_3)_{n-}$, wherein $R^1$ is selected from the group consisting of hydrogen and hydrocarbons, in particular hydrogen and C1-C12 hydrocarbons, more in particular hydrogen and C1-C12 alkyls, and wherein n is 1, 2, 3 or 4;
  L is a spacer ligand, in particular a spacer ligand comprising a radical R comprising q carboxylate groups ($—COO^-$), wherein, q is 1, 2, 3, 4, 5 or 6, preferably 2, 3 or 4. R may in particular be selected from the group consisting of C1-C12 alkyl, C2-C12 alkene, C2-C12 alkyne, mono- and poly-cyclic C6-C50 aryl, mono- and poly-cyclic C3-C50 heteroaryl and organic radicals comprising a metal material selected from the group consisting of ferrocene, porphyrin, phthalocyanine and Schiff base $R^{X1}R^{X2}—C=N—R^{X3}$, wherein $R^{X1}$ and $R^{X2}$ are independently selected from the group consisting of hydrogen, C1-C12 alkyl, C2-C12 alkene, C2-C12alkyne and mono- and poly-cyclic C6-C50aryl and wherein $RX3$ is selected from the group consisting of C1-C12 alkyl, C2-C12 alkene, C2-C12 alkyne and mono- and poly-cyclic C6-C50 aryl.

Such MOF's have been described in WO 2009/130251 of which the contents are incorporated by reference, in particular with respect to the definitions $M_nO_kX_iL_p$, at page 2 line to page 5, line 19. These MOF's may in particular be used for a sensor for detecting a sulphur containing compound.

The amount of particles in the coating, is usually in the range of 0.1-10 vol %, preferably in the range of 1-5 vol %.

The invention further relates to a blend material, comprising
  a polymer comprising a chain having an aromatic group and a group selected from the group of sulfonyl groups, carbonyl groups, carbonate groups, imide groups, fluorocarbon groups, siloxane groups, pyridine groups and amide groups; and
  particles composed of material that is capable of absorbing the analyte.

The blend material may in particular be present as coating or part thereof on a waveguide, more in particular a waveguide of a sensor system as described herein. In a particular embodiment, the particles are elastomeric nanoparticles and/or MOF nanoparticles.

With the term 'blend material', is meant a material that is a blend of a polymeric material and particles. With this term is also meant to be understood a material wherein the particles are bonded chemically with the polymer molecules.

Preferred embodiments for the blend material are as described above for the polymers/particles.

The invention further relates to the use of a sensor system for detecting in an environment at least one analyte selected from the group of alkanes (such as methane, ethane, or propane), carbon dioxide, hydrogen sulfide, hydrogen, water, carbon monoxide, oxygen, hydrogen cyanide and ammonia.

The invention further relates to a method for preparing a waveguide, in particular a waveguide according to the invention, comprising
  providing a waveguide,
  preferably pretreating the waveguide with a silanisation agent,
  applying a mixture, comprising a solvent and a coating composition comprising polymer or a precursor thereof, to at least part of the surface of the waveguide, and
  curing the coating composition, whereby the solvent is at least substantially evaporated or the precursor is reacted.

In an embodiment, the mixture that is applied comprises elastomeric nanoparticles.

In an advantageous method of the invention, the waveguide or at least a part thereof to be coated is placed in a mould, leaving a space between the outer surface of the waveguide or part thereof inside the mould and the inner surface of the mould, introducing the coating composition into the space; and curing the coating composition.

It is possible to coat a selected part of the waveguide. Such part is not limited to an extremity of the waveguide. One or more parts remote from the extremities can be selectively coated.

By using a coating composition already comprising the polymer a coating can be provided without needing to include curing agents, initiators and the like, although this is in principle possible, in particular in case the polymer in the coating should be crosslinked.

The present application further is directed to a waveguide, which waveguide comprises a core and a cladding at least partially covering the core, wherein, in a cross-sectional plane that is perpendicular to the longitudinal direction of the waveguide, the thickness of the cladding in a first radial direction in said plane is different from the thickness of the cladding in a second radial direction in said plane and to a sensor system comprising such a waveguide.

Such a sensor system may also be used under extreme conditions, such as under conditions that may exist in underground oil or gas reservoirs, or in the equipment that is used to produce oil or gas from these reservoirs. Thus, such a sensor system may be provided with a coating as described above, or used as an alternative solution to overcome problems recognised by the present inventors that may occur under extreme conditions, as. e.g. may exist in underground oil or gas reservoirs.

With a radial direction is meant a direction from a central point. In case the cross-section of the core has a circular shape, the central point is the centre of the circle. In case the cross-section of the core has an elliptical shape, the central point is the centre of the ellipse, i.e. the cross-point of the minor axis of the ellipse with the major axis of the ellipse. In case the cross-section of the core has the shape of a polygon with rotational symmetry, such as a triangle or a square, the central point is the centre of that polygon. With rotational symmetry of a polygon is meant that a polygon fits onto itself after a turn of less than 360° around its centre.

A waveguide in a sensor according to the invention usually comprises a grating, in particular a fibre Bragg grating or a long period grating.

In a multiplexed sensor system, the waveguide comprises two or more gratings, e.g. two or more fibre Bragg gratings, two or more long period gratings, or a combination comprising at least one fibre Bragg grating and at least one long period grating.

There are different embodiments of a waveguide wherein the thickness of the cladding in a first radial direction in the cross-section is different from the thickness of the cladding in a second radial direction.

Figure 2:
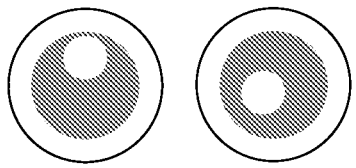

In an embodiment, the centre of the circular cross-section of the cladding does not coincide with the centre of the circular cross-section of the core (FIG. 2).

Figure 3:
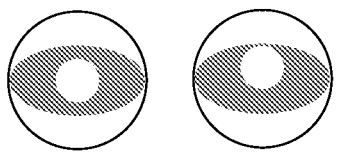

In another embodiment, the cross-section of the cladding is non-circular, e.g. elliptical, while the cross-section of the core is circular (FIG. 3).

Figure 4:
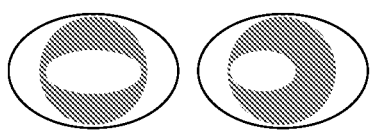

In yet another embodiment, the cross-section of the core is non-circular, e.g. elliptical, while the cross-section of the cladding itself is circular (FIG. 4).

Figure 5:
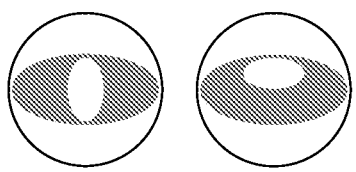

In yet another embodiment, the cross-section of the core as well as the cross-section of the cladding is non-circular, e.g. elliptical (FIG. 5).

Figure 6:
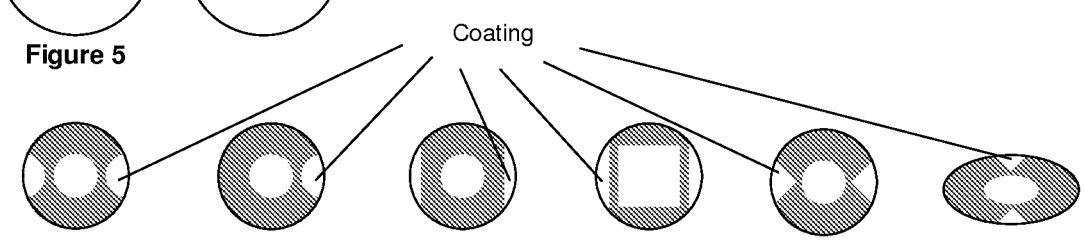

In yet another embodiment, the cross-section of the cladding has another design than those represented in FIGS. 1-5. Some of such cross-section designs are shown in FIG. 6. In these designs the coating is present on a specific location of the waveguide where the cladding is thinner or absent, e.g. in the carves, while locations where the cladding is thicker are not coated or are coated with a coating that has a smaller thickness than the coating on a location of the waveguide where the cladding is thinner or absent.

A specific cross-section design, e.g. a design as shown in any of the FIGS. 2-6, is present along at least a section of the waveguide. Such section of the waveguide usually comprises a grating. A specific cross-section design may also extend along a section of the waveguide where no gratings are present, and even along the entire waveguide.

Usually, a coating that is capable of deforming under the influence of the environmental effect is present on those areas of the cladding where the cladding is thinner or absent. Preferably, on those areas of the cladding where the cladding is thicker, such coating is absent or a thinner coating of the same kind as that used on a thinner cladding is present. It is also possible to provide a different coating on those areas of the cladding where the cladding is thicker.

Bragg reflection in a waveguide depends on the optical properties of the core, the cladding and the coating. The thickness of the cladding determines the penetration depth of the electromagnetic radiation in the coating. If the cladding is thick enough the electromagnetic radiation (evanescent field) will not penetrate into the coating. For example, generally no significant penetration occurs when the cladding has a thickness of more than 5 µm, in particular of more than 10 µm. Usually, the thickness of the cladding is about 50 µm when it is desired that no penetration occurs. A thickness of the cladding of less than 5 µm, in particular of less than 1 µm, may for example be used to effect a substantial penetration of electromagnetic radiation into the coating. More in particular, no cladding is present. The diameter of the core is not critical. and may for instance be in the range of 1-100 µm, in particular in the range of 5-25 µm, e.g. about 10 µm The coating is designed to change a dimension (in particular in the longitudinal direction) and/or the optical properties of the waveguide under the influence of (a change in) an environmental effect.

In particular, the sensor system comprising a waveguide wherein, in a cross-sectional plane that is perpendicular to the longitudinal direction of the waveguide, the thickness of the cladding in a first radial direction in said plane is different from the thickness of the cladding in a second radial direction in said plane preferably comprises a source for providing a first beam of polarized electromagnetic radiation having the plane of polarization perpendicular to said first radial direction, and a second beam of polarized electromagnetic radiation, having the plane of polarization perpendicular to said second radial direction.

The angle between the two radial directions is more than 0° and less than 180°. In particular, the angle between the directions is in the range of 15°-165°, more in particular the angle is in the range of 30°-150°, or in the range of 60°-120°. In practice, it is preferred that the directions are perpendicular.

When the plane of polarisation of a beam is perpendicular to the radial direction wherein the cladding is thicker than the cladding in another radial direction, the Bragg-reflection is mainly affected by the dimensions and optical properties of the core-cladding combination. When the plane of polarisation of the other beam is perpendicular to the radial direction wherein the cladding is thinner than the cladding in another radial direction (or wherein the cladding is absent), and when on the areas of thinner (or absent) cladding a coating is present, the Bragg-reflection is mainly affected by the dimensions and optical properties of that core-cladding-coating combination. Thus, it can be achieved that the light of one plane of polarization may be mainly subject to the dimensions and optical properties of the core-cladding combination, and the light of the other plane of polarization mainly to the dimensions and optical properties of the core-cladding-coating combination, while the physical period of the grating for both waveguide configurations is the same.

In an embodiment, the thickness of the cladding of the waveguide in each radial direction is equal to the thickness in the radial direction opposite thereto, or at least does not differ significantly from that direction. Such embodiments are for example represented by the cross-section designs that are present most left in each of the FIGS. 3-6.

In another embodiment the thickness of the cladding in a certain radial direction is significantly different from the thickness in the radial direction opposite thereto. Such embodiments are for example represented by the cross-section designs that are present most right in the each of the FIGS. 2-5, and by the second cross-section design from the left in FIG. 6. Such cross-sections, i.e. cross-sections wherein the requirement of a thin cladding is met on only one of two opposite sites side may also provide the effect described hereinabove, i.e. the effect that Bragg-reflection is mainly affected by the dimensions and optical properties of core-cladding-coating combination.

Accordingly, the sensor system, which may be multiplexed, allows the simultaneous measurement of two environmental effects with one grating, by distinguishing the Bragg reflections in the two polarisation directions. This is for example advantageous when one wants to correct for the influence of temperature on the optical properties of the waveguide when measuring the environmental effect, for example $H_2S$ in an underground reservoir, or another effect such as mentioned above. Compensation for the influence of the temperature by simply performing a calibration at a specific temperature is generally not sufficient, because temperatures may vary over time and place.

An embodiment with a temperature sensor system as described hereinabove may advantageously be used under extreme conditions, such as under conditions that may exist in underground oil or gas reservoirs, or in the equipment that is used to produce oil or gas from these reservoirs.

A suitable coating may be selected from the group of coatings as described hereinabove.

Further, a suitable coating may in particular be selected from materials as described in the yet to be published European patent application EP07150214.0 of which the contents are incorporated by reference, in particular with respect to details about the coating. An example of a material disclosed herein is a material comprising a polymer comprising an aliphatic chain, which aliphatic chain is provided with functional, preferably hydrophilic, side-chains comprising at least one moiety selected from the group of heterocycloalkyl moieties; in particular, in such a coating the heterocycloalkyl moiety comprises at least one heteroatom selected from the group of nitrogen, sulphur and oxygen, and more in particular, the heterocycloalkyl moiety is selected from the group of morpholine moieties, pyrrolidone moieties, pyrrolidine moieties, oxazolidine moieties, piperidine moieties, tetrahydrofuran moieties, tetrahydropyran moieties, piperazine moieties and dioxane moieties. Further details can be obtained from the application of which the number is given above.

Further, a suitable coating may in particular be selected from materials as described in the yet to be published European patent application EP07150481.5 of which the contents are incorporated by reference, in particular with respect to details about the coating. For the coating a sensor material may be used comprising a polymer having internal stress, which polymer is capable of at least partially relaxing under the influence of the environmental effect; In a specific embodiment, the polymer having internal stress comprises cross-links, which crosslinks are adapted to be cleaved under the influence of the environmental effect; such cross-links may in particular be selected from the group of amide group cross-links, ester group cross-links, complexed metal ion cross-links, saccharide-based crosslinks, Diels-Alder-based cross-links, diazidostilbene-based cross-links and diperoxide-based cross-links. Further details can be obtained from the application of which the number is given above.

Further, a suitable coating may in particular comprise a material that changes colour and/or refractive index due to (a change in) an environmental effect. Such materials may for example be selected from the group of transition metal complexes, porphyrines and phtalocyanines. The invention will now be illustrated by the following examples.

EXAMPLE 1

A 25 wt % polycarbonate solution was made by dissolving 20.0 g of polycarbonate (PC, Lexan® LR3958) in 60.0 g of dichloromethane. A 25 wt % polysulfone solution was prepared by dissolving 4.0 g of polysulfone (PSU, Ultrason S2010®) in 12.0 g of dimethylacetamide. The solutions were stirred for 12 hours until clear solutions were obtained. Two acrylic coated Fibre Bragg Grating (FBG) glass fibres were stripped of the acrylic coating. One fibre was dipped twice in the polycarbonate solution and one fibre was dipped twice in the polysulfone solution using a dipcoater to generate a uniform coating and both were cured in an oven at 60° C. The dipcoat speed was 2 mm/s for PSU and 7 mm/s for PC. A coating layer of 50-70 μm was deposited on the fibres. The two fibres were spliced to prepare a single fibre having two sensors. The maximum wavelength of the reflected light was 1534.85 nm for PC and 1529.80 nm for PSU.

The two coated gratings were exposed simultaneously to an increasing concentration of $H_2S$ in air. Using a FOS&S Spectraleye 600 interogator, the change in reflected maximum wavelength was monitored during the exposure to $H_2S$ gas. The final concentration of $H_2S$ was 90%. After exposure the chamber was flushed with dry air in order to remove the hydrogen sulfide gas. The changes in reflected maximum are shown in FIG. 7 for both the PSU coated grating and the PC coated grating.

EXAMPLE 2

A series of polysulfone imide sensor polymers was prepared by the reaction of a sulfonyl diamine with a dianhydride. Two diamines and two dianhydrides were used. In Table 1, the molecular formulae of these four compounds are shown.

TABLE 1 diamines and dianhydrides for preparation of sensor coating

Diamine I 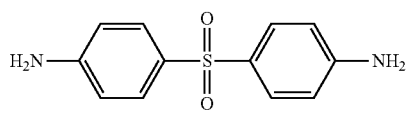 [SMILES: Nc1ccc(S(=O)(=O)c2ccc(N)cc2)cc1]

TABLE 1-continued diamines and dianhydrides for preparation of sensor coating

Diamine II: H₂N—C₆H₄—O—C₆H₄—S(O)₂—C₆H₄—O—C₆H₄—NH₂

Dianhydride I: pyromellitic dianhydride

Dianhydride II: 3,3',4,4'-diphenylsulfone tetracarboxylic dianhydride

One of the diamines was dissolved in N-methyl pyrrolidon (NMP) (20 wt %) and one of the dianhydrides was dissolved in NMP (20 wt %), with the exception of dianhydride I which was dissolved in dimethylsulfoxide (DMSO) (20 wt %). After dissolution, the two solutions were mixed under a nitrogen atmosphere and the polymer solution was obtained. Acrylic coated Fibre Bragg Grating (FBG) glass fibres were stripped of the acrylic coating on the grating over a distance of approximately 20 a 30 mm. The stripped fibres were pretreated with a silane coupling agent (γ-aminopropyltriethoxysilane) and cured for 180 minutes at 120° C. The fibres were then dipped in the polysulfone-imide solution to obtain the chemical sensor.

EXAMPLE 3

To create a sensor to detect $H_2S$ gas, a fibre with a fibre Bragg grating was coated with a $H_2S$-sensitive coating. The coating consists of a polysulfoneimide binder formulation with Pebax® as a sensitive component. Pebax® is a polyether block amide and is heat- and UV-resistant. Pebax® swells when placed in contact with $H_2S$ gas. The Pebax® material was added to the coating as particles with a size in the range of 1-5 μm.

0.252 g of a Pebax® elastomer (2533SN01) was mixed with 10.03 g of NMP. Under stirring, the NMP-Pebax® mixture was heated in a glass bottle by an oil bath to 140° C. (the temperature being measured in the NMP/Pebax® mixture), yielding a brown liquid. After melting the Pebax®, 0.25 g of Byk 104S (a surfactant) was added. While still being heated, the mixture was stirred by an Ultra Turrax set at 20500 min$^{-1}$ for approximately 5 minutes. The bottle with the mixture was removed from the heating bath and stirred again with the Ultra Turrax for a two minutes. After cooling the bottle to room temperature, it contained a brown dispersion.

The dispersion was visualized by light microscopy (FIG. 2). The particles differed in size from approximately 1 to 10 μm. The variation in particle size was decreased by filtration.

The Pebax® dispersion was added to a polysulfone or polyimide solution prepared according to Example 2, to obtain a blend polymeric material comprising nanoparticles.

EXAMPLE 4

To create a sensor to detect $CO_2$ gas, a fibre with a fibre Bragg grating was coated with a $CO_2$-sensitive polyimide coating. One of the diamines (III-VI) was dissolved in N-methyl pyrrolidone (NMP) (20 wt %). One of the anhydrides (III-IV) was added as a solid to the solution (equimolar amount). The mixture was put under a nitrogen atmosphere and mixed at room temperature for 18 hours. During polymerisation the anhydride dissolved and a clear solution was obtained. Commercial polyimide coated Fibre Bragg Grating (FBG) glass fibres (Optolink) were stripped of the polyimide coating on the grating over a distance of approximately 20 a 30 mm. The stripped fibres were pretreated with a silane coupling agent (γ-aminopropyltriethoxysilane) and cured for 180 minutes at 120° C. Using a Vytran recoater, the new sensor polyimide coating was applied in thin layers, to obtain the chemical sensor.

In Table 2, the molecular formulae of the six compounds are shown.

TABLE 2 diamines and dianhydrides for preparation of $CO_2$ sensor coating

Diamine III: H₂N—(CH₂)₃—Si(CH₃)₂—O—[Si(CH₃)₂—O]ₙ—Si(CH₃)₂—(CH₂)₃—NH₂ n = 0 or 8

TABLE 2-continued diamines and dianhydrides for preparation of CO$_2$ sensor coating Diamine IV 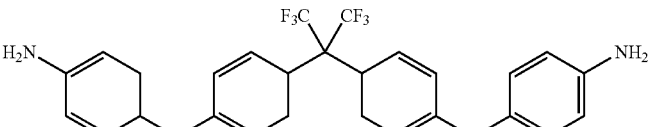

Diamine V 

Diamine VI 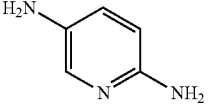

Dianhydride III 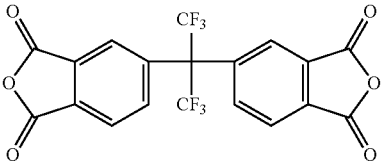 [SMILES: O=C1OC(=O)c2cc(S(=O)(=O)c3ccc4c(c3)C(=O)OC4=O)ccc21]

Dianhydride IV 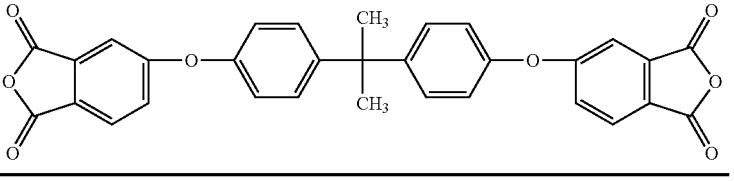

The invention claimed is:

1. A sensor system comprising a waveguide, which waveguide comprises a grating in at least a part of the waveguide, which waveguide further comprises a coating, the coating comprising a polymer, which polymer comprises a chain, in which chain are present an aromatic group and a chemical group selected from the group of sulfonyl groups, carbonyl groups, carbonate groups, siloxane groups, pyridine groups, organofluorine groups and amide groups.

2. A sensor system according to claim 1, wherein the chain further comprises imide groups.

3. A sensor system according to claim 1, wherein the chain further comprises oxygen atoms.

4. A sensor system according to claim 1, wherein the polymer is:
a polysulfone, such as a poly (diphenyl sulfone), and preferably poly(oxy-1,4-phenylenesulfonyl-1,4-phenyleneoxy-1,4-phenyleneisopropylidene-1,4-phenylene), or poly(4,4'-(sulfonylbis(4,1-phenyleneoxy)) dianiline-co-4,4'-(sulfonyl) diphthalic anhydride), or a polycarbonate, such as a poly(diphenyl carbonate), and preferably poly(oxycarbonyloxy-1,4-phenyleneisopropylidene-1,4-phenylene), or
a polyimide, such as an aromatic fluorocarbon polyimide, and preferably poly(4,4'-(hexafluoro-isopropylidene) dianiline-co-4,4'-(hexafluoro-isopropylidene) diphthalic anhydride) or poly(2,5 diamino pyridine -co-4,4'-(hexafluoro-isopropylidene) diphthalic anhydride), or
a polyamide, preferably poly(trimellitic anhydride chloride-co-4,4'-diaminodiphenylsulfone), or
a polysiloxane, preferably poly (1,3-bis(3-aminopropyl) tetramethyldisiloxane-co-4,4'-(hexafluoro-isopropylidene) diphthalic anhydride).

5. A sensor system according to claim 1, wherein the grating is a fibre Bragg grating, and wherein the waveguide comprises a plurality of gratings that are spatially apart, preferably 2-100 gratings that are spatially apart.

6. A sensor system according to claim 1, wherein the coating further comprises absorbent particles.

7. A sensor system according to claim 6, wherein the coating comprises absorbent particles selected from the group of elastomeric particles.

8. A sensor system according to claim 6, wherein the elastomeric absorbent particles comprise a copolymer of a polyether and a polyamide or an organofluorine composition.

9. A sensor system according to claim 6, wherein the coating comprises absorbent particles selected from the group of metal organic framework particles.

10. A sensor system according to claim 1, wherein the polymer coating on the waveguide has a thickness of 0.5 μm to 200 μm, preferably of 10 to 100 μm, more preferably of 20 to 50 μm.

11. A sensor system according to claim 1, further comprising a source for providing electromagnetic radiation, and a photo-detector.

12. A waveguide, comprising a grating in at least a part of the waveguide, which waveguide comprises a coating, the coating comprising a polymer, which polymer comprises a chain having an aromatic group and a group selected from the group of sulfonyl groups, carbonyl groups, carbonate groups, siloxane groups, organofluorine groups, pyridine groups and amide groups.

13. A waveguide according to claim 12, wherein said chain further comprises imide groups or oxygen atoms and/or wherein the grating is a fibre Bragg grating.

14. Use of a sensor system according to claim 1 for detecting in an environment at least one analyte selected from the group of alkanes (e.g. methane, ethane, propane), carbon dioxide, hydrogen sulphide, hydrogen, water, carbon monoxide, oxygen, hydrogen cyanide and ammonia.

15. Use of a sensor system according to claim 1 for the detection of one or more environmental effects on two or more spatially distinct sites, wherein the waveguide comprises a multitude of gratings, at least part of which are present as pairs, in which pairs the first grating is used to measure a certain environmental effect, and the second grating is uncoated or is coated with a coating that is insensitive, or at least not sensitive to a measurable extent, to the environmental effect to be measured with the first grating.

16. Use of a sensor system according to claim 1 for measuring an environmental effect under non-ambient conditions, in particular under conditions that may exist in underground oil or gas reservoirs, or in the equipment that is used to produce oil or gas from these reservoirs.

\* \* \* \* \*